# United States Patent
Kim et al.

(10) Patent No.: US 8,759,103 B2
(45) Date of Patent: Jun. 24, 2014

(54) POLYNUCLEOTIDE DELIVERING COMPLEX FOR TARGET CELL

(75) Inventors: Won Jong Kim, Pohang-si (KR); Do Won Hwang, Incheon (KR); Dong Soo Lee, Seoul (KR); Se Jin Son, Pohang-si (KR)

(73) Assignee: Postech Academy-Industry Foundation, Pohang-Si, Kyungsangbuk-Do (KR)

( * ) Notice: Subject to any disclaimer, the term of this patent is extended or adjusted under 35 U.S.C. 154(b) by 0 days.

(21) Appl. No.: 13/321,093

(22) PCT Filed: Aug. 25, 2011

(86) PCT No.: PCT/KR2011/006299
§ 371 (c)(1),
(2), (4) Date: Nov. 17, 2011

(87) PCT Pub. No.: WO2012/081799
PCT Pub. Date: Jun. 21, 2012

(65) Prior Publication Data
US 2013/0330826 A1    Dec. 12, 2013

(30) Foreign Application Priority Data
Dec. 15, 2010   (KR) ........................ 10-2010-0128622

(51) Int. Cl.
*C12N 15/00* (2006.01)
*A61K 47/34* (2006.01)

(52) U.S. Cl.
CPC ...................................... *A61K 47/34* (2013.01)
USPC ............ 435/455; 435/458; 530/358; 530/395

(58) Field of Classification Search
CPC .................. C12N 15/85; C12N 15/87; C12N 2810/6081; A61K 47/34
USPC .................................................. 435/455, 458
See application file for complete search history.

(56) References Cited

FOREIGN PATENT DOCUMENTS

WO    WO 2010/089122 A2 *   8/2010

OTHER PUBLICATIONS

Son, Sejin, et al. "RVG peptide tethered bioreducible polyethylenimine for gene delivery to brain", Journal of Controlled Release, Issue 155 (2011), pp. 18-25, Elsevier B.V.
Yang Liu, et al., "Brain-targeting gene delivery and cellular internalization mechanisms for modified rabies virus glycoprotein RVCG29 nanoparticles", Biomaterials, vol. 30, 2009, pp. 4195-4202.
Korean Office Action for Application No. 10-2010-0128622, dated Sep. 18, 2012 and English Translation.
S.D. Laufer et al., "Peptide-Mediated Cellular Delivery of Oligonucleotide-Based Therapeutics in Vitro: Quantitative Evaluation of Overall Efficacy Employing Easy to Handle Reporter Systems", Current Pharmaceutical Design, vol. 14, 2008, pp. 3637-3655.

* cited by examiner

*Primary Examiner* — Janet Epps-Smith
(74) *Attorney, Agent, or Firm* — Kile Park Reed & Houtteman PLLC

(57) ABSTRACT

The present invention provides a polynucleotide delivery system including a cationic polymer to which a rabies virus glycoprotein (RVG) peptide is bound, wherein the cationic polymer includes a biodegradable bond, and a method of delivering polynucleotides to a target cell by using the delivery system.

13 Claims, 9 Drawing Sheets

POLYNUCLEOTIDE DELIVERING COMPLEX FOR TARGET CELL

TECHNICAL FIELD

Figure 1A:
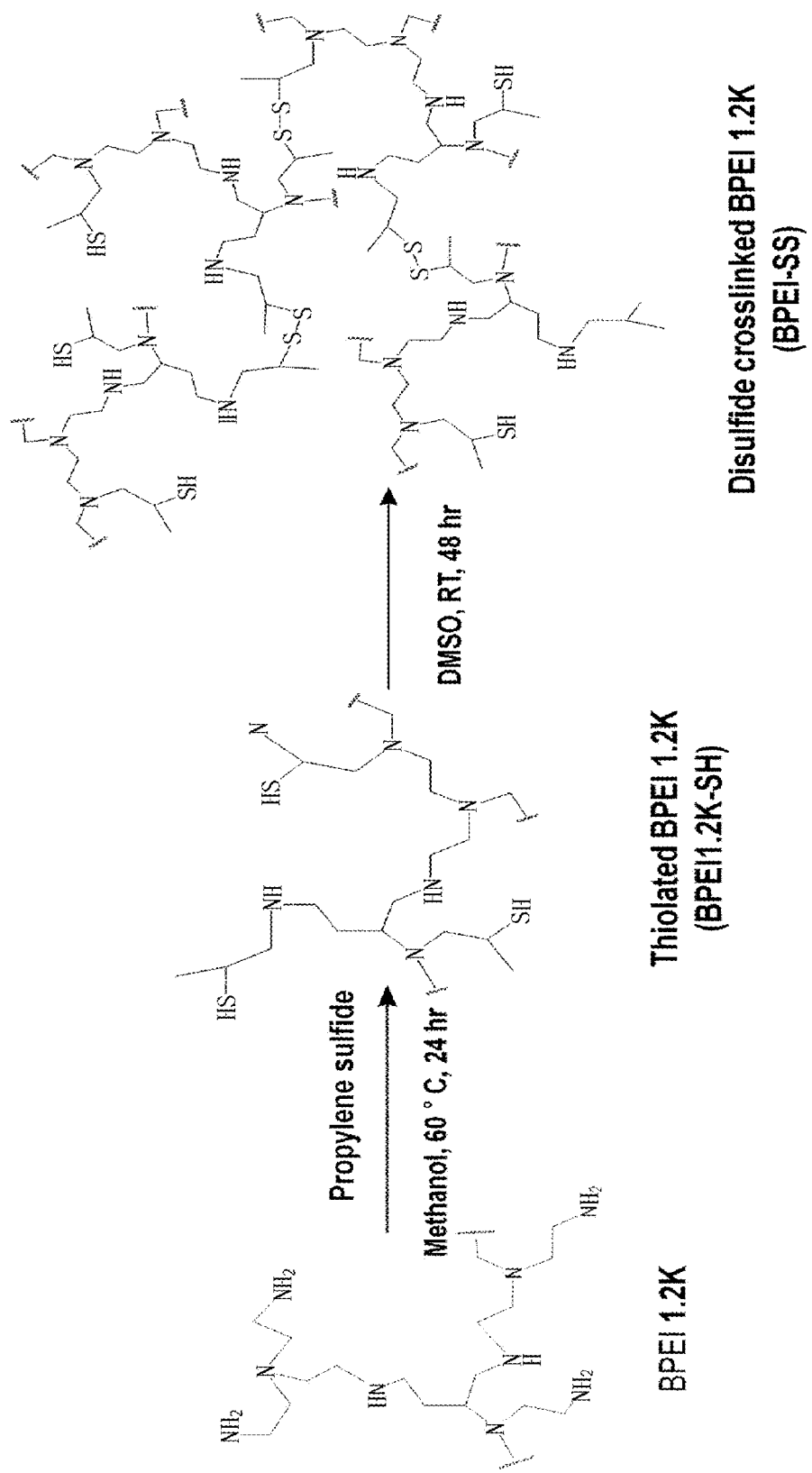

This application claims the benefit of Korean Patent Application No. 10-2010-0128622, filed on Dec. 15, 2010, in the Korean Intellectual Property Office, the disclosure of which is incorporated herein in its entirety by reference.

The present invention relates to a polynucleotide delivering complex for a target cell.

BACKGROUND ART

Gene therapy refers to the correction of genetic defects by injecting a new gene constructed by using a DNA recombinant method into cells of a patient, or to the prevention or treatment of genetic defects such as cancer by genetic modification of cells, infectious diseases or autoimmune diseases by adding new functions to the cells. However, because polynucleotides including genes may be easily cleaved by degrading enzymes present in cells and cellular membranes and polynucleotides are all strongly negatively charged, it is very difficult for polynucleotides to pass through cellular membranes to be delivered to cells. The efficiency of polynucleotides to be introduced into cells is very low and thus much research on gene delivery systems for delivering polynucleotides has been actively conducted in order to address these problems.

As a delivery system for delivering polynucleotides into target cells, viral and non-viral delivery systems may be used. Although viral delivery systems have high transfection efficiency, there are limitations in applying the systems to humans due to disadvantages in that their manufacturing processes are complex and the systems have safety issues such as immunogenicity, infection potential, inflammation production, insertion of non-specific polynucleotides, etc. and there are limitations in terms of the sizes of polynucleotides that can be accommodated.

Accordingly, non-viral delivery systems have been recently highlighted as a replacement for viral delivery systems. Non-viral delivery systems are advantageous in that a minimal immune response may lead to repeated administration, a specific delivery to a specific cell may be allowed, and mass production may be easily achieved. Among non-viral delivery systems, cationic polymers which allow a polynucleotide-polymer complex to be formed through ionic bonding to polynucleotides which are negatively charged have been recently highlighted. For example, the cationic polymers include poly-L-lysine, polyethyleneimine, poly[α-(4-aminobutyl)-L-glycolic acid], etc., and these pressurize polynucleotides to form nanoparticles and protect polynucleotides from enzymatic cleavage, and are rapidly penetrated into cells to aid in exiting from endosomes. In particular, it is well known that polyethylene imine effectively pressurizes plasmid DNA to be made into colloidal particles and has high polynucleotide delivery efficiency due to a buffering capability of pH reactivity to effectively deliver polynucleotides in vitro and in vivo to a variety of cells.

However, as conventional cationic polymers have increased molecular weights, interaction with polynucleotides increases and thus the polymers are stably introduced into cells. An extremely strong interaction prevents polynucleotides from being efficiently released and polynucleotides are introduced in the form of a complex into a nucleus, which causes toxicity or lowers polynucleotide delivery efficiency. In addition, these cationic polymers interact with plasma proteins present in blood or are removed by reticuloen-dothelial system, the stability of the cationic polymers in blood is so low that it is difficult to use in practically clinical applications.

In particular, a blood brain barrier (BBB) is a membrane which protects the central nerve system and has a compact structure that prevents external materials from being easily introduced, and thus it is difficult to deliver drugs and genes due to limited permeability.

Thus, there is a need for a reducible polynucleotide delivery system which provides long-lasting circulation and safety in blood, exhibits efficient polynucleotide delivery efficiency, and has low toxicity. In addition, there is a need for a polynucleotide delivery system which may introduce polynucleotides into brain cells in order to treat neurodegenerative diseases.

DISCLOSURE OF INVENTION

Technical Problem

The present invention provides a polynucleotide delivery system including a cationic polymer to which a rabies virus glycoprotein (RVG) peptide is bound.

Solution to Problem

The present invention provides a polynucleotide delivery system including a cationic polymer to which a rabies virus glycoprotein (RVG) peptide is bound, wherein the cationic polymer includes a biodegradable bond, and a method of delivering polynucleotides to a target cell by using the delivery system.

According to an aspect of the present invention, there is provided a polynucleotide delivery system including a cationic polymer to which an RVG peptide is bound, wherein the cationic polymer includes a biodegradable bond selected from the group consisting of an ester bond, an amide bond, a disulfide bond, a phosphate bond, and a combination thereof.

The "polynucleotide delivery system" delivers a specific polynucleotide to a target cell, and may be used for gene therapy.

As used herein, the term "gene therapy" refers to the correction of defective genes by introducing normal genes or therapeutic genes into target cells that require gene therapy, or the prevention or treatment of genetic defects through genetic modification of cells by adding new functions to the cells. The target cell to be subjected to gene therapy is any cell requiring gene therapy, and may include a mammalian cell such as human, cow, pig, mouse, rat, goat, hamster, sheep, and horse, or an avian cell, etc. In addition, the gene therapy may be applied to a variety of states or target cells. The target cell may include, but is not limited to, a normal cell, a cancer cell, a tumor cell, a primary culture cell, a stem cell, etc.

As used herein, the term "polynucleotide" refers to a polymer of deoxyribonucleotides or ribonucleotides, in the form of a single strand or a double strand. The polynucleotide may be any polynucleotide which may express a protein in a target cell, may include a portion of RNA genomic sequence, DNA (gDNA and cDNA) and a portion of RNA sequence transcribed therefrom, or siRNA, etc. and may include analogues of a natural polynucleotide unless otherwise specifically stated.

In addition, genes which may be included in the polynucleotide may include, but is not limited to, normal genes of a target gene related to a disease, expression inhibitory genes of target proteins, for example, cancer therapeutic genes which induce apoptosis of cancer cells and ultimately degenerate tumors, tumor inhibitory genes, immune regulatory genes, cytokine genes, antigenic genes, suicide genes, cytotoxic genes, cell proliferation inhibitory genes, pro-apoptotic genes, and anti-angiogenic cells. Furthermore, various therapeutic genes which may be usefully used for treatment of various diseases may be delivered by a complex according to a specific embodiment. They may include, for example, genes encoding cytokine, interleukin, chemokine, or a colony stimulating factor, genes expressing tissue plasminogen activator (tPA) or urokinase, lysosomal acid lipase (LAL) producing genes which provide continuous antithrombotic effect to prevent cholesterol hyperlipidemia, etc. They may also include cystic fibrosis, adenosine deaminase deficiency, virus such as AIDS, and various polynucleotides for treatment of malignant and inflammatory diseases and states. A base sequence of the gene or polynucleotide may be obtained from a base sequence database such as GenBank or EMBL.

The delivery system may include a cationic polymer to which an RVG peptide is bound, wherein the cationic polymer includes a biodegradable bond selected from the group consisting of an ester bond, an amide bond, a disulfide bond, a phosphate bond, and a combination thereof.

According to a specific embodiment of the present invention, the RVG peptide may also include variants of an RVG peptide, and polypeptide fragments or derivatives. More specifically, the RVG peptide may include an amino acid sequence of SEQ ID NO. 1.

The RVG peptide may bind to an acetylcholine receptor expressed in a target cellular membrane to allow the polynucleotide delivery system to be delivered to a target cell. The target cell may include, but is not limited to, an acetylcholine receptor, homologues thereof, or a cell expressing polypeptide fragments thereof, for example, neurons, blood brain barrier (BBB) cells, etc.

According to a specific embodiment of the present invention, the RVG peptide may bind to an acetylcholine receptor expressed in a BBB to allow the polynucleotide delivery system of the present invention to pass through the BBB. The polynucleotide delivery system of the present invention may pass through the BBB to deliver polynucleotides into cells inside the BBB, for example, central nerve system cells. Examples of the central nerve system cell may include, but are not limited to, neurons, brain cells, glials, astrocytes, and neuronal supporting cells.

According to a specific embodiment of the present invention, the cationic polymer may include, but is not limited to, polyethyleneimine (PEI), poly-L-lysine (PLL), chitosan, dendrimer, etc.

The polyethyleneimine is one of a plurality of delivery systems that have high delivery efficiency, may be classified into branched and linear forms, and may be synthesized with various molecular weights. A branched form may be applied to a delivery system with various forms and functions according to the branching ratio. A branched polyethyleneimine (BPEI) may be used as the cationic polymer.

The poly-L-lysine may be synthesized with various sizes and molecular weights. Poly-L-lysine is connected through a biodegradable peptide bond and thus may be applied in vivo and form nano-complexes with polynucleotides to be in vivo delivered. However, poly-L-lysine exhibits some degree of toxicity and thus there is a limitation in exhibiting high delivery efficiency alone. In order to overcome the limitation, endosome destruction materials or endosomal fusion peptides, etc. may be attached to exhibit high delivery efficiency.

The chitosan has a β-1,4 binding of pyranose monomers of glucosamine, 5000 or more of glucosamine residues and a molecular weight of 1,000,000 or more. The chitosan is a polysaccharide-based biopolymer having polyvalent cations and may be extracted from marine origins including shells of crustacean such as crabs, shrimps, etc. and squids. Its molecular structure reveals that chitosan has a structure similar to that of cellulose which is a kind of polysaccharide. Chitosan has excellent biocompatibility and does not cause any rejection during its immune reaction. In particular, it is known that a chitosan with a specific molecular weight in the range of 20,000 to 100,000 exhibits strong physiological functions.

The dendrimer refers to a macromolecular compound in which branched unit structures repeatedly stretch from a central molecule, and has a structure sterically similar to a sphere. The dendrimer structurally has many functional groups at its ends, facilitating the attachment of peptides which aid in permeation of cell specific materials or nuclear membranes or materials which aid in escaping from endosomes.

The biodegradable bond refers to a bond which allows a starting material to be converted into a less complex intermediate or final product by solubilization hydrolysis or action of an enzyme or biological organism, etc. The cationic polymer of the present invention may include, but is not limited to, an ester bond, an amide bond, a disulfide bond, a phosphate bond, or a combination thereof. A polymer including the bond may be cleaved into its lower molecular weight forms, producing less toxicity in the cell.

According to a specific embodiment of the present invention, the cationic polymer of the polynucleotide delivery system may include a disulfide bond. When the polynucleotide delivery system is delivered inside the cell, the disulfide bond may be broken to release polynucleotides included due to a difference in concentrations of glutathione (GSH) in and out of the cell.

According to a specific embodiment of the present invention, there is provided a polynucleotide delivery system which further includes a non-peptidic polymer between the RVG peptide and the cationic polymer. The RVG peptide of the present invention may bind to the cationic polymer through a non-peptidic polymer.

The non-peptidic polymer may be selected from the group consisting of polyethylene glycol, polypropylene glycol, copolymers of ethylene glycol and propylene glycol, polyoxyethylated polyols, polyvinyl alcohol, polysaccharides, dextran, polyvinyl ethyl ether, polylactic acid (PLA), poly-lactic-glycolic acid (PLGA), lipid polymers, chitins, hyaluronic acid, and a combination thereof, but it is not limited thereto. Derivatives thereof, which are well known in the art and easily prepared within the skill of the art, are included in the scope of the present invention.

According to a specific embodiment of the present invention, there is provided a polynucleotide delivery system to which polyethylene glycol is bound between the RVG peptide and the cationic polymer.

According to a specific embodiment of the present invention, the cationic polymer includes a disulfide bond, and the RVG peptide provides a polynucleotide delivery system including an amino acid sequence of SEQ ID NO. 1.

According to a specific embodiment of the present invention, there is provided a polynucleotide delivery system further including a polynucleotide selected from the group consisting of gDNA, cDNA, pDNA, mRNA, tRNA, rRNA, siRNA, miRNA, and antisense nucleotide.

The polynucleotide to be bound to the delivery system comprehensively includes DNA, RNA, and synthesized homologues thereof. Examples of the polynucleotide may include, but are not limited to, gDNA, cDNA, plasmid DNA (pDNA), mRNA, tRNA, rRNA, siRNA, miRNA, and antisense nucleotides. They may be naturally present or synthesized, and may be vary in size, ranging from oligonucleotide to chromosome. These polynucleotides originate from human, animals, plants, bacteria, viruses, etc. These may be obtained by methods well known in the art.

According to another aspect of the present invention, there is provided a method of delivering polynucleotides to a target cell, the method including: binding polynucleotides to the polynucleotide delivery system; and contacting the delivery system to which the polynucleotide is bound with the target cell.

The method may include binding polynucleotides to a delivery system for delivering the polynucleotide to the target cell.

The bond may be achieved by electrostatically binding a negatively charged polynucleotide to be introduced to a target cell in a cationic polymer of the delivery system.

Nitrogen in a cationic polymer in the delivery system is positively charged under in vivo conditions (for example, pH 7.4). In addition, a phosphor acidic group in the polynucleotide is negatively charged under the conditions and thus the bond may be achieved by electrostatic attraction between the cationic polymer and the polynucleotide.

When the delivery system is used as an in vivo delivery system of a polynucleotide, the expression efficiency of genes in the polynucleotide may be greatly affected by the delivery system, the mixture ratio of the polynucleotide, and the nitrogen/phosphate (N/P) ratio. When the N/P ratio increases, the polynucleotide may be more condensed in the complex, the overall polynucleotide is positively charged, and thus it may be delivered into the cell with high efficiency. However, as the N/P ratio increases, the expression efficiency may be reduced and the toxicity may be increased, and thus the N/P ratio should be appropriately controlled during the binding. According to a specific embodiment of the present invention, the weight ratio of the delivery system to polynucleotide may be, for example, 0.1 to 20, or 0.1 to 10.

The method may include contacting a delivery system to which the polynucleotide is bound with a target cell.

The contacting may be performed in vitro or in vivo. When the contacting is performed in vivo, the method may include administrating a delivery system to which the polynucleotide is bound into a subject.

The subject may be a cell, a tissue, an organ or an individual. In addition, the administration may be performed by dissolving a delivery system to which the polynucleotide is bound in an appropriate buffer to directly contact the delivery system with the cell, the tissue or the organ, or parenterally administering the delivery system to the individual. When the administration is performed parenterally, the polynucleotide may be administered intravenously, subcutaneously, intramuscularly, intraperitoneally, intradermally, topically, intranasally, intrapulmonarily, and intrarectally. The delivery system to which the polynucleotide is bound includes a ligand for a target cell and thus polynucleotides may be delivered to a target cell to be administered by the method.

The delivery of polynucleotides by the delivery system is performed by receptor-mediated endocytosis. In other words, when the delivery system is contacted with a target cell by the method, a ligand in the delivery system binds to a receptor in the target cell to introduce the delivery system to which the polynucleotide is bound into the target cell. For example, polynucleotides may produce a desired protein in the target cell through expression of a gene in the polynucleotide to affect the target cell.

According to a specific embodiment of the present invention, the target cell which contacts the delivery system may include, but is not limited to, an acetylcholine receptor (AchR) and homologues thereof, or a cell in which polypeptide fragments thereof are expressed. For example, it may include an α-subunit of AchR or homologues thereof, or a cell in which fragments thereof are expressed.

BRIEF DESCRIPTION OF DRAWINGS

The above and other features and advantages of the present invention will become more apparent by describing in detail exemplary embodiments thereof with reference to the attached drawings in which:

FIG. 1a and FIG. 1b are a synthesis schemes of a polynucleotide delivery system for a target cell;

FIG. 2 is a graph illustrating a result of a $^1$H nuclear magnetic resonance (NMR) spectrum about disulfide-containing branched poly(ethyleneimine)-polyethylene glycol-rabies virus glycoprotein (BPEI-SS-PEG-RVG);

FIG. 3a and FIG. 3b are graphs illustrating a change in size (FIG. 3a) and a change in surface potential (FIG. 3b) of a complex according to a weight ratio of a polynucleotide delivery system (polymer/pDNA);

FIG. 4a and FIG. 4b are graphs illustrating a change in size (FIG. 4a) and a change in surface potential (FIG. 4b) of a polynucleotide delivery system/polynucleotide complex according to a concentration of a serum protein;

FIG. 5a and FIG. 5b are graphs illustrating experimental results which evaluate the toxicity of a polynucleotide delivery system/pDNA (polymer/pDNA) for a Neuro2a cell. A graph of FIG. 5a exhibits the toxicity of a polynucleotide delivery system/pDNA complex according to the weight ratio and a graph of FIG. 5b exhibits the toxicity of a polynucleotide delivery system/pDNA complex over time;

FIG. 6a and FIG. 6b are images and a graph illustrating experimental results which evaluate the polynucleotide delivery efficiency of a BPEI-SS-PEG-RVG/polynucleotide complex. FIG. 6a includes confocal microscope images of Neuro2a and HeLa cells and FIG. 6b exhibits the delivery efficiency of polynucleotides according to the polynucleotide delivery system; and FIG. 7a and FIG. 7b images and a graph illustrating experimental results which evaluate an in vivo target directivity of a polynucleotide delivery system/polynucleotide complex for a target cell. FIG. 7a exhibits organs removed from a mouse treated with a polynucleotide complex and FIG. 7b exhibits the expression efficiency of genes in the brain region according to the polynucleotide delivery system.

MODE FOR THE INVENTION

Hereinafter, the present invention will be described in more detail with reference to specific Examples. However, these Examples are provided only for illustrating one or more specific Examples and should not be construed as limiting the scope of the present invention.

[Experimental Material and Method]

Materials and experimental methods used in Examples of the present specification are as follows.

1. Material

A branched polyethyleneimine (molecular weight (MW): 25,000, branched polyethyleneimine (BPEI) 25K), propylene sulfide (methyl thiirane), propylene ethylene glycol monomethyl ether (methoxy polyethylene glycol (PEG) or (MPEG), MW: 5000), and 4-nitrophenyl chloroformate (4-NPC) were purchased from Sigma-Aldrich (St. Louis, USA), BPEI (MW: 1200, BPEI 1.2K) was purchased from Polyscience, Inc. (War-rington, PA), and N,N-dimethylformamide (DMF)

was purchased from Acros (Ceel, Belgium). Dimethyl sulfoxide (DMSO) was purchased from Burdick and Jackson (Honeywell International Inc., USA), heterobifunctional polyethylene glycol and α-maleimide-ω-N-hydroxy-succinimide ester polyethylene glycol (MAL-PEG-NHS, MW: 5000) were purchased from NOF Corporation (White Plains, N.Y., USA), and rabies virus glycoprotein (RVG) peptide (Sequence: YTIWM-PENPRPGTPCDIFTNSRGK-FRASNG) was purchased from AnyGen, Inc. (Korea).

2. Cell Culture and Preparation of Plasmid DNA (pDNA)

Neuro2a and mouse neuroblastoma cell lines were purchased from American Type Culture Collection (ATCC) and cells were typically incubated in a culture medium supplemented with 10% fetal bovine serum (FBS) (Invitrogen, Grand Island, N.Y., USA), 10 U/mL penicillin (Invitrogen, Grand Island, N.Y.), and 10 μg/mL of streptomycin in a 5% CO2 humidified chamber.

pDNA used for luciferase activity analysis in Examples 3 to 5 and 6 was prepared by amplifying a firefly luciferase coding sequence region by polymerase chain reaction (PCR) to insert the region into a pcDNA3.1(+) vector (Invitrogen, Grand Island, N.Y.) including a cytomegalovirus (CMV) promoter by using Hind III and Xho I restriction enzyme sites and then cloning the vector (CMV-Fluc).

pDNA used for an experiment to observe how much red fluorescent protein (RFP) was expressed in Example 6 (FIG. 6a) and used in Example 7 was manufactured by inserting a red fluorescence protein into a pcDNA3.1(+) vector including a CMV promoter and then cloning the vector (CMV-RFP).

3. Statistical Analysis

The results were expressed as average±standard error of mean (SEM). An unpaired T-test was used to perform statistical analysis between two groups.

EXAMPLE 1

Figure 1B:
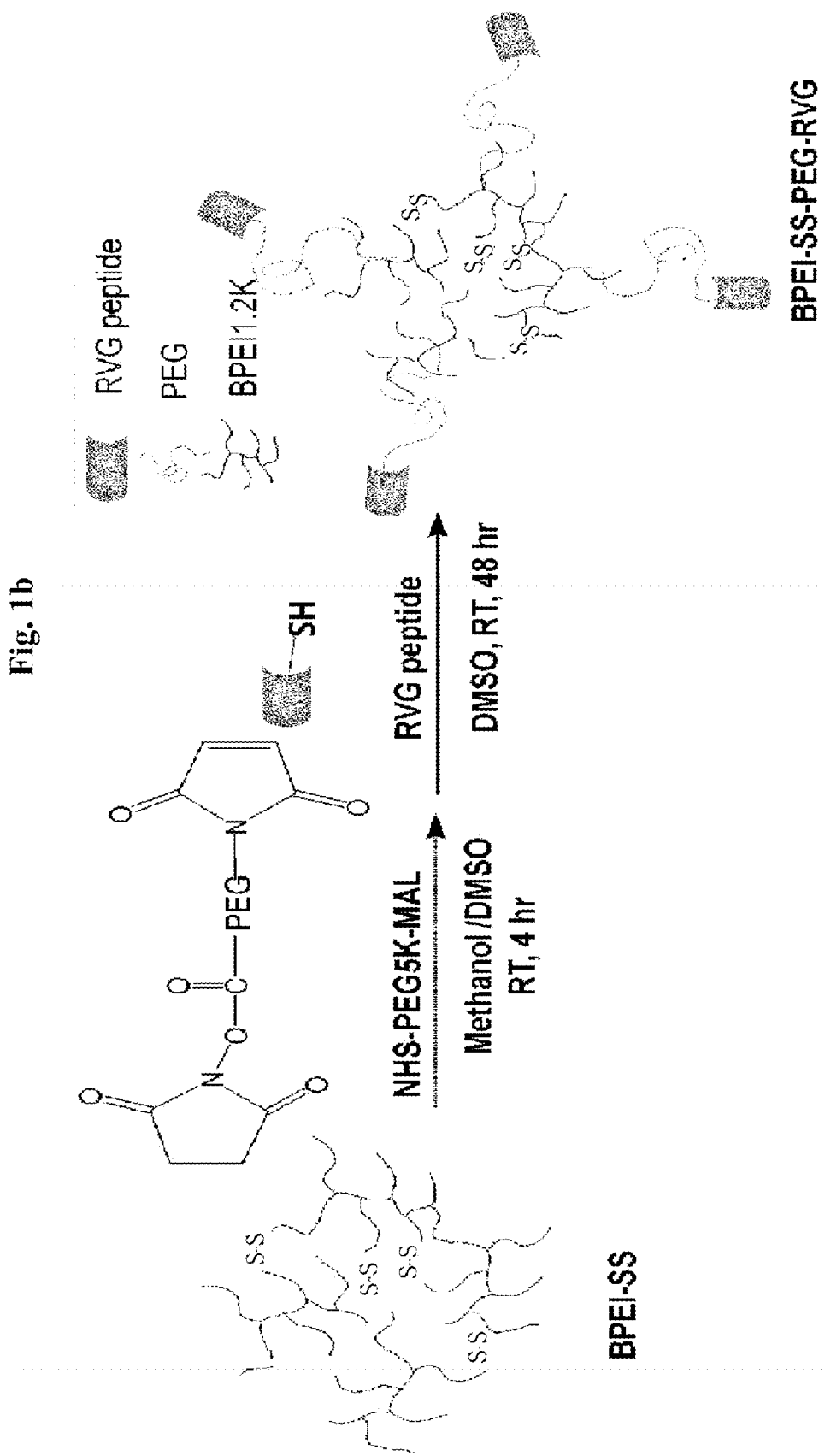

Synthesis of Polynucleotide Delivery System 1 g of branched polyethyleneimine (BPEI, MW: 1200) was dissolved in 100 ml of distilled water, the pH was adjusted to 7.2, and then the solution was lyophilized for 2 days. 1 g of a yellow lyophilized yellow solid was dissolved in 30 ml of ethanol, the solution was placed in a round-bottom flask, and nitrogen filling and vacuum conditions were repeated 5 to 6 times. 5 and 10 excess mole numbers of propylene sulfide were added to this, allowed to react for 24 hrs while the temperature was maintained at 60° C., precipitated three times in ice-cold diethyl ether, and the residual solvent was removed in a vacuum oven for 1 day to synthesize thiolated BPEI 1.2K (FIG. 1).

Subsequently, 1.2 g of BPEI-SH was reacted under the oxidation conditions of 100 ml of DMSO for 48 hrs to synthesize a BPEI-SS into which a disulfide bond was introduced, and 0.25 g of NHS-PEG-MAL and 20 mg of RVG peptide were sequentially added to allow them to react for 6 hrs. Through this, a polynucleotide delivery system for a target cell was synthesized (BPEI-SS-PEG-RVG) (FIG. 1).

EXAMPLE 2

Figure 2:
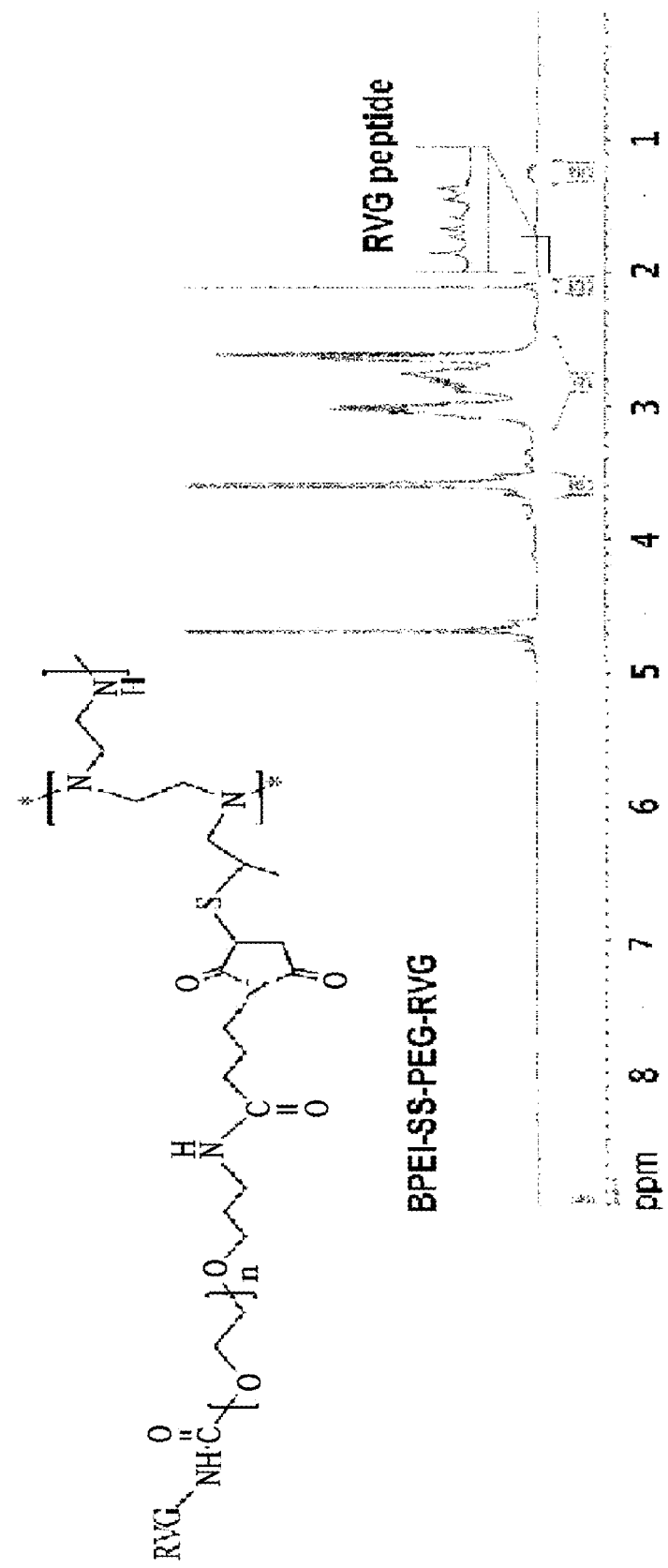

Analysis of Synthesized Polynucleotide Delivery System $^1$H NMR (Brucker BioSpin 2002) was used to analyze the amount of PEG included in BPEI (PEG: 3.5 to 4.2 ppm, BPEI: 3.15 to 2.55 ppm. FIG. 2), and an area ratio was used to confirm that one PEG had been introduced in 11.2 of BPEI 1.2K. In addition, it was confirmed that a thiol group had been introduced into BPEI 1.2K through a hydrogen peak of a methyl group in propylene sulfide conjugated to BPEI at 1.5 ppm.

Tryptophan in residues of RVG peptide absorbs light at 280 nm and emits it at 355 nm, these properties were used to observe the amount of RVG peptides introduced into BPEI through a fluorescence method, and it was confirmed that one RVG had been conjugated to 19.7 of BPEI 1.2K.

EXAMPLE 3

Formation of Polynucleotide Delivery System/Polynucleotide Complex and Evaluation of Physical and Chemical Properties 1) Formation of Polynucleotide Delivery System/Polynucleotide Complex In order to evaluate a capability of BPEI-SS-PEG-RVG to form an effective complex and provide protection against degradation, a gel retardation assay was performed. Each of BPEI-SS-PEG-RVG and BPEI-SS was mixed with 200 ng of pDNA in a Dulbecco's Phosphate-Buffered Saline (DPBS) buffer solution at different mixture ratios to form 20 μl of a final solution, and the mixture was left for 30 min to bind a polynucleotide delivery system to a polynucleotide. Subsequently, 12 μl of the mixture was loaded to perform a gel retardation assay. As a result, each BPEI-SS and BPEI-SS-PEG-RVG effectively formed a complex with pDNA at low weight ratios (delivery system/pDNA) of 0.6 and 0.75, respectively, while unthiolated BPEI 1.2K formed a complex at a higher weight ratio of 1.3 (data not shown).

2) Physical and Chemical Properties of Polynucleotide Delivery System/Polynucleotide Complex In order to evaluate physical and chemical properties of a BPEI-SS-PEG-RVG/polynucleotide complex, a size and surface potential of a complex were measured by varying the mixture ratio of the delivery system and polynucleotide (FIG. 3). The mixture ratios of each of BPEI-SS-PEG-RVG, BPEI-SS, and BPEI 1.2K with pDNA (1 μg) were varied to form 20 μl of each complex, to which 1 ml of DPBS was added, 1 ml of each resulting mixture was placed in respective cuvettes, and each cuvette was placed in a surface charge measuring device (Zetasizer Nano S: Malvern Instruments, Malvern, UK) to measure the surface charge. In addition, the same sample was placed in a size measuring device (Zetasizer Nano Z: Malvern Instruments, Malvern, UK) to measure the size.

Figure 3A:
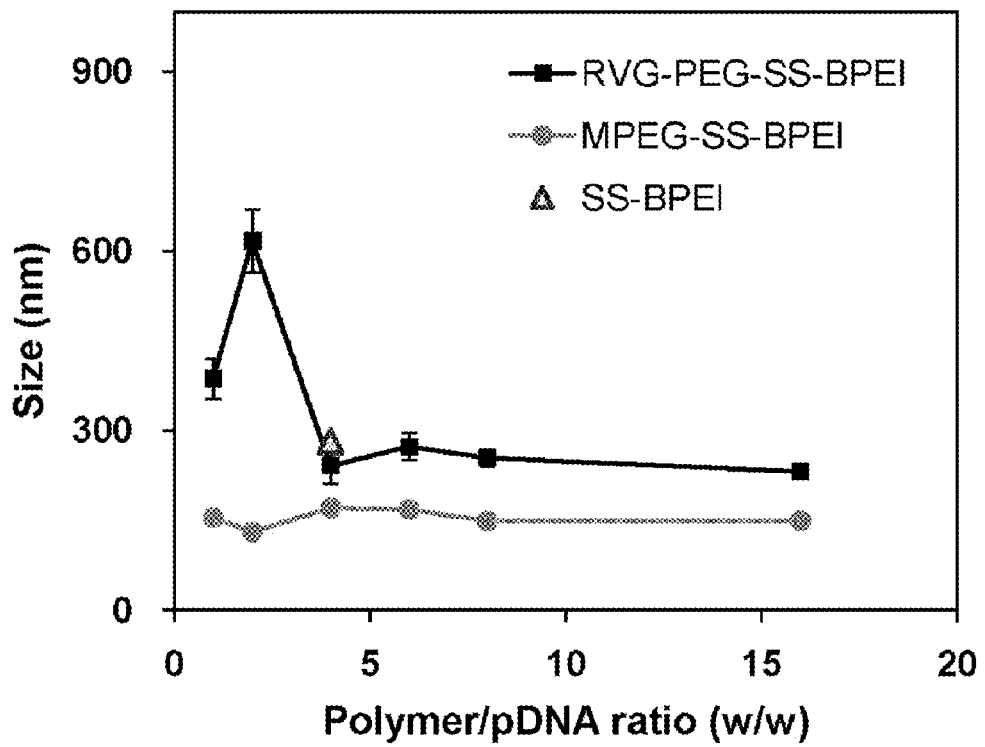
Figure 3B:
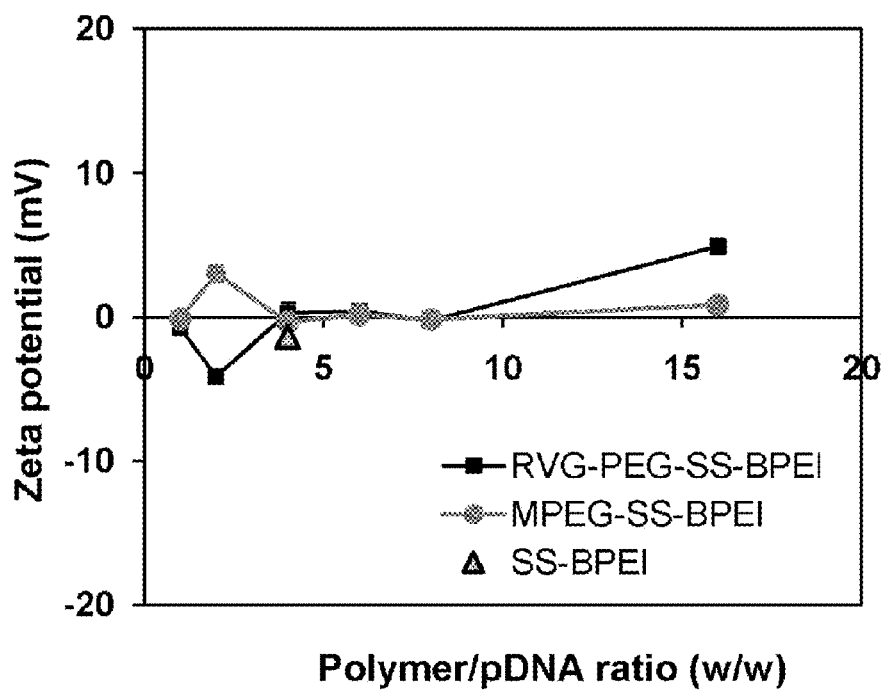

As the weight ratio of BPEI-SS-PEG-RVG/pDNA complex to pDNA increased from 1 to 2 compared to the delivery system, the particle size increases. However, the size is stably maintained to about 230 nm at a weight ratio of 4 or more. Through this, it was confirmed that the complex might interact with polynucleotide effectively to form stable particles (FIG. 3a). In addition, it was confirmed that the BPEI-SS-PEG-RVG/pDNA complex had a surface potential close to 0, and thus it was determined that the BPEI-SS-PEG-RVG/polynucleotide complex might be maintained as a very stable particle in an in vivo environment (FIG. 3b).

EXAMPLE 4

Colloidal Stability of Synthesized Polynucleotide Delivery System/Polynucleotide Complex When BPEI was circulated through the blood vessel in a living organism, the BPEI was rapidly degraded by a reticuloendothelial system due to its strong cationic properties, which is a limitation. Thus, PEG with a hydrophilic property was introduced. However, the insufficient screening of cationic properties may allow a cationic polymer to non-specifically interact with components in blood to induce a rapid removal from the circulation system. Thus, the colloidal stability was measured.

Each of BPEI-SS-PEG-RVG and BPEI-SS formed a complex with 1 μg of pDNA at a ratio of 8:1, and the complex was added to serum in RPMI at different concentrations of 1 ml to measure the size and surface potential of the complex according to the analysis method in Example 3.

Figure 4A:
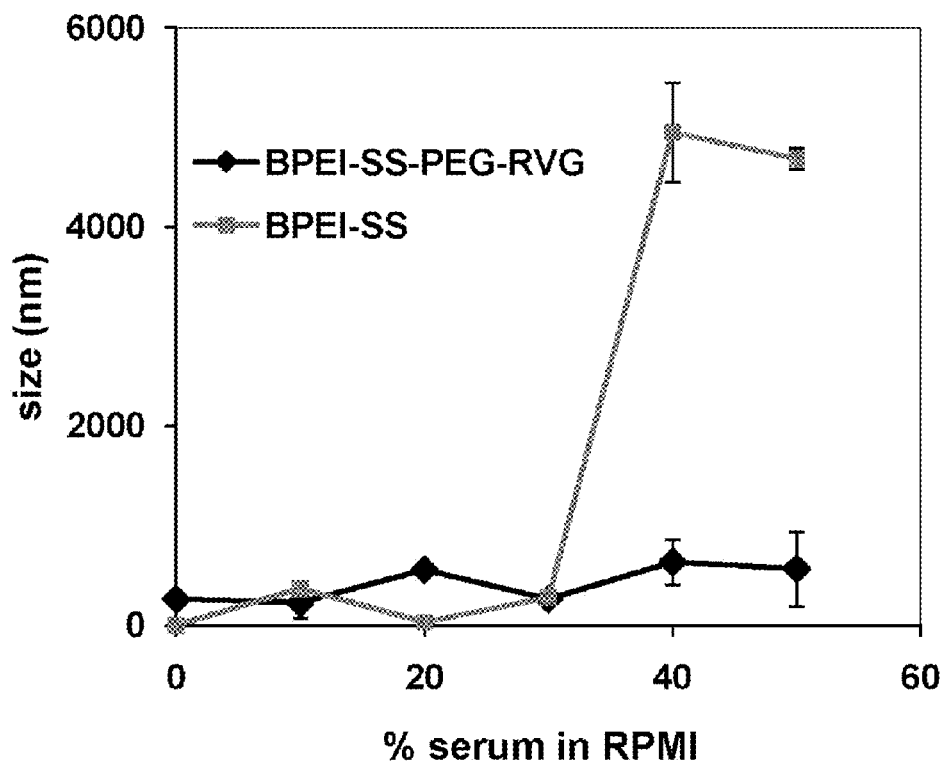
Figure 4B:
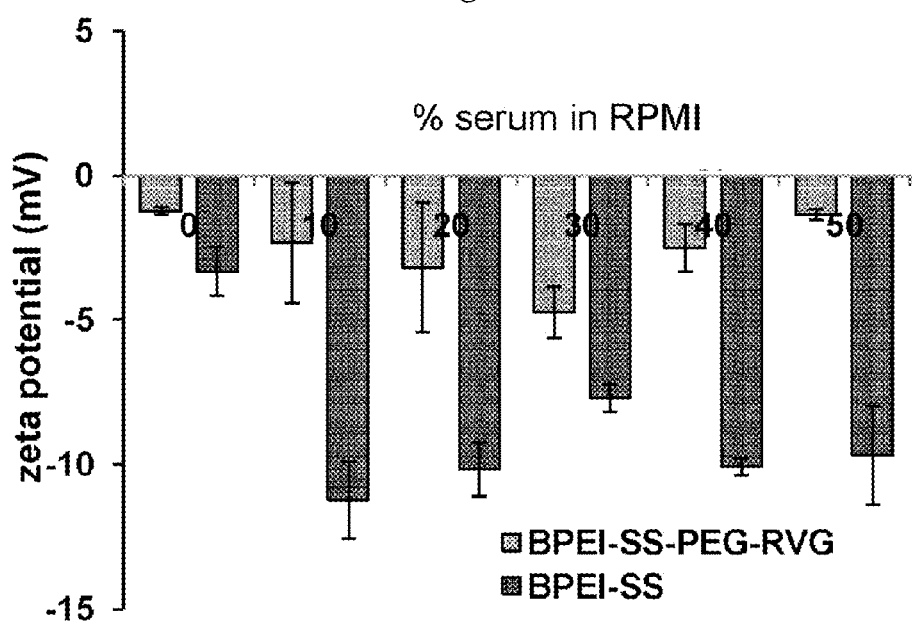

When the serum concentration of BPEI-SS as a reducible polymer without PEG increased from 0% to 40%, the size of the delivery system/polynucleotide complex increased from 300 nm up to 5000 nm, while the size of the delivery system/polynucleotide complex was constantly maintained in BPEI-SS-PEG-RVG with PEG even though its serum concentration increased by 10% to 50% (FIG. 4a). It was determined through this that the stability of the BPEI-SS-PEG-RVG/polynucleotide complex might be maintained in blood for a long time. In addition, the BPEI-SS-PEG-RVG exhibited a surface potential close to neutrality in serum, and thus it was confirmed that a non-specific interaction with proteins in blood might be prevented (FIG. 4b).

EXAMPLE 5

Cytotoxicity Evaluation of Synthesized Polynucleotide Delivery System/Polynucleotide Complex A methyl tetrazolium (MTT) assay was used to evaluate the toxicity of a BPEI-SS-PEG-RVG/polynucleotide complex produced on cells (FIG. 5). The toxicity of a BPEI-SS/pDNA complex on neuro2a cells was investigated at various weight ratios, and an irreducible and high-molecular weight BPEI 25K was used as a control.

The MTT analysis method is a test method which uses the capability of mitochondria to reduce 3-(4,5-dimethylthiazol-2-yl)-2,5-diphenyltetrazolium bromide (MTT) as a yellow aqueous substrate into a purplish non-aqueous MTT-formazan crystal by dehydrogenases of mitochondria of living cells, and may measure the proliferation behavior of cells in great numbers rapidly and exactly.

Neuro2a cells in which an acetylcholine receptor was expressed were inoculated to α-MEM medium in a 96-well microplate ($1 \times 10^4$ cells/well) and incubated at 37° C. in a 5% CO2 incubator for 24 hrs. Each of BPEI 25K and BPEI-SS formed a complex with 0.4 μg of pDNA for 30 min prior to use at different mixture ratios. A complex formed and 100 μl of a serum-free medium were treated together with Neuro2a cells, and the medium solution was replaced with 200 μl of a medium solution supplemented with 10% serum to incubate cells for 21 hrs. Next, the MTT solution (20 μl, 5 mg/mL) was introduced, the cells were incubated for another 4 hrs, the medium was reduced, and 150 μl of DMSO was introduced into each well to dissolve the purplish formazan crystal formed through reaction with cells. 100 μl was aliquoted from each well and placed in a 96-well plate prepared. A microplate spectrofluorometer (VICTOR 3 V Multilabel Counter, Perkin Elmer-Wellewleym MA, USA) was used and the optical density (OD) was measured at a wavelength of 570 nm to compare the cytotoxicity results according to the mixture ratio of the complex for analysis.

In addition, in order to observe the cytotoxicity over time, an experiment was performed at a weight ratio of a delivery system/polynucleotide in the complex at 4:1 in the same manner as in the above Examples. However, cytotoxicity results were obtained in the same manner as in the above Examples, except for replacing the medium solution with 200 μl of a medium solution supplemented with 10% serum and performing incubation for 24 and 48 hrs, respectively.

Figure 5A:
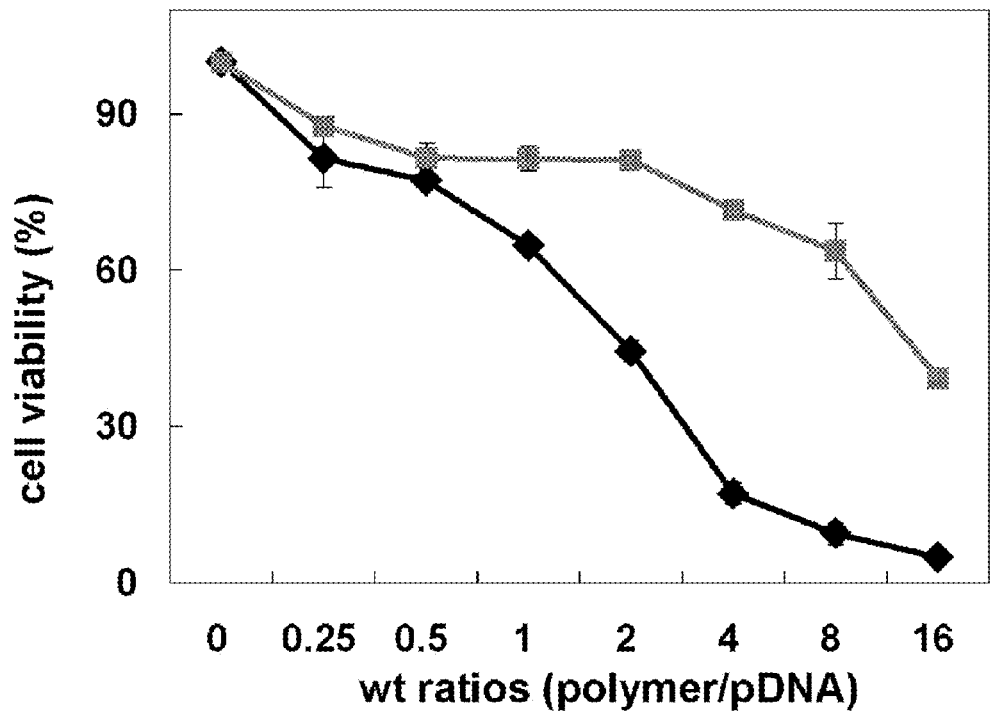
Figure 5B:
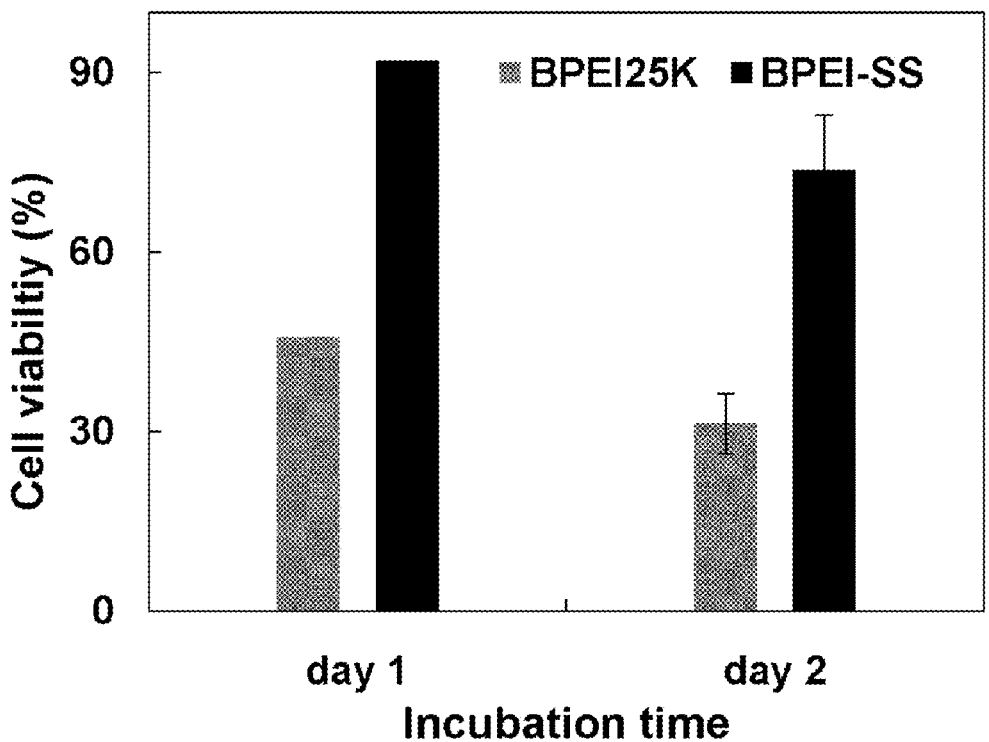

The irreducible and low molecular weight BPEI 25K exhibited higher toxicity than that of a reducible BPEI-SS at a weight ratio of the overall delivery system/pDNA used in the experiment, and caused toxicity of such severity that the death of cells was promoted particularly at a weight ratio of 1 to kill 80% or more of total cells. On the contrary, it was confirmed that the reducible BPEI-SS exhibited 80% or more of cell viability at the weight ratio of pDNA (0 to 2), compared to a delivery system used for delivery of polynucleotide (FIG. 5a). In addition, the BPEI 25K/pDNA complex exhibited 40% cell viability based on the total cells after one day, while the reducible BPEI-SS/pDNA complex exhibited 90% cell viability based on the total cells (FIG. 5b). Based on these results, it is believed that the reducible polynucleotide delivery system allows a disulfide bond to be broken by glutathione (GSH) in a cell and a polynucleotide delivery system which has been degraded into low molecular weight molecules causes less toxicity.

EXAMPLE 6

Figure 6A:
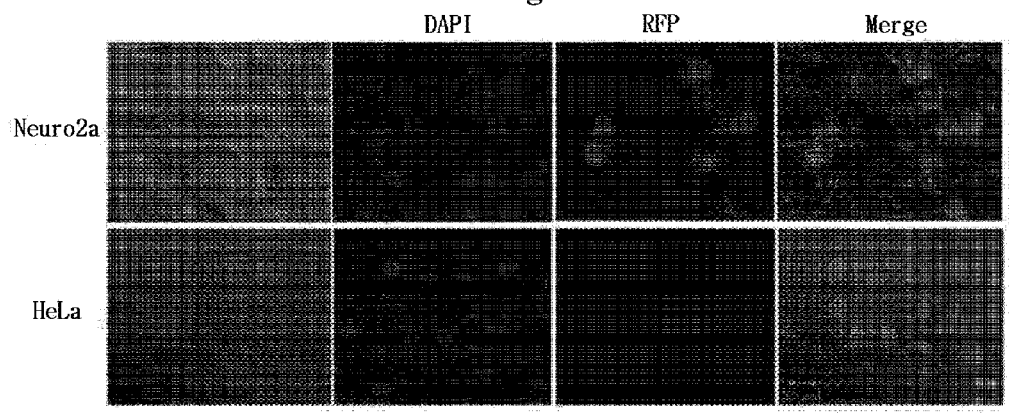

Evaluation of Polynucleotide Delivery Efficiency of Synthesized Polynucleotide Delivery System/Polynucleotide Complex A BPEI-SS-PEG-RVG/polynucleotide complex was treated with Neuro2a cells, in which an acetylcholine receptor that selectively recognizes the RVG peptide is expressed, and HeLa cells, in which the acetylcholine receptor is not expressed, to evaluate the polynucleotide delivery efficiency from the degree of RFP expression by using a confocal microscope (FIG. 6a).

Neuro2a and HeLa cells were sequentially inoculated on a 12-well plate on a sterilized coverslip. Cells were incubated with a delivery system/pDNA complex (delivery system 4 μg and pDNA 1 μg) for 24 hrs and then washed twice with a DPBS solution. Cells were mixed with 3.7% formaldehyde solution (Sigma, Saint Louis, Mo.) for 20 min and then washed three times with DPBS. Cells attached to cover slices of a 12-well plate were introduced into a previously treated mounting solution (Vector Laboratories, Inc, CA) including 4',6-diamidino-2-phenylindole (DAPI) solution on a slide glass. Confocal microscopic images obtained by using a Zeiss LSM examiner The excitation wavelength used for DAPI imaging was HFT 405/488 and other detailed conditions were as follows: pinhole diameter: 98 μm and filter: BP 420-480 IR. Numerical values for RFP imaging were HFT 488/543 nm (wavelength), 96 μm (pinhole diameter), and LP 560 (filter).

Red fluorescence indicates RFP and blue fluorescence (stained with DAPI) indicates stained nucleus. Under the same conditions as above, it was observed that Neuro2a cells had higher intensity of red fluorescence than that of HeLa cells. Thus, it was determined that the BPEI-SS-PEG-RVG/polynucleotide complex had been effectively introduced into cells for gene expression.

Figure 6B:
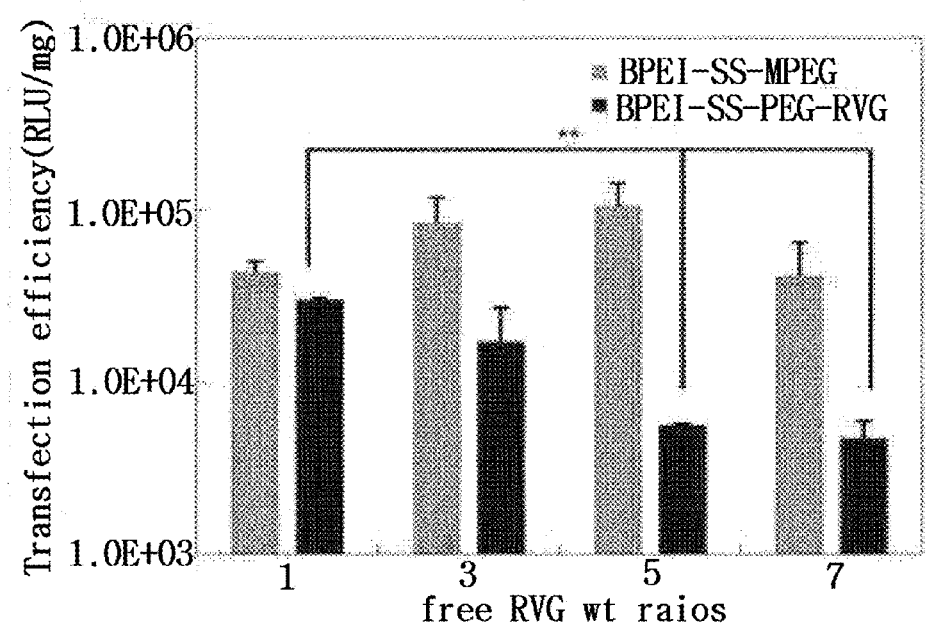

In addition, in order to evaluate the targeting capability of a synthesized polynucleotide delivery system, a competitive inhibition assay with free RVG was performed by using PEI-SS-MPEG as a negative control (FIG. 6b).

All transient transfections were performed in triplicate. Neuro2a cells were inoculated on a 24-well plate for inhibition analysis and washed twice with DPBS, and 200 μl of Opti-MEM medium (Gibco) was added to each well plate. From 10 min prior to use, the free RVG was added to the Neuro2a cells in a dose-dependent manner (free RVG concentrations: 2, 6, 10, and 14 μg) for incubation and washed twice with PBS. BPEI-SS-PEG-RVG (or BPEI-SS-MPEG) and CMV-Fluc pDNA were mixed at a weight ratio of 4:1 and treated on each well plate. After 24 hours of the complex treatment, luciferase analysis was performed.

A firefly luciferase activity was analyzed by using a luciferase analysis kit (Applied Biosystems). Neuro2a cells with the complex treated for 24 hrs as described above were washed twice with DPBS solution and lysed by using a Triton X-100 based lysis solution. Subsequently, all of the cell lysate was collected and placed in a 96-well microplate such that air bubbles were not introduced into the well. The bioluminescence signal was measured by using a 96-well microplate luminometer (TR717; Applied Biosystems) and setting the exposure time at 20 sec.

FIG. 6b shows that 2, 6, 10, and 14 μg of free RVG were added at weight ratios of 1, 3, 5, and 7, respectively. When NeuroRo2a cells were pre-incubated with an excess of RVG peptide, the genetic expression of a BPEI-SS-PEG-RVG/pDNA complex was progressively inhibited from Neuro2a cells as the amount of free RVG peptide increased. However, although a large amount of free RVG peptide was used, the genetic expression of the BPEI-SS-MPEG/pDNA complex was not inhibited. When 14 μg of RVG peptide was present in the medium, the genetic expression was reduced in Neuro2a cells by almost 6.4 times. This demonstrates that free RVG peptide and an RVG motif on the surface of BPEI-SS-PEG-RVG/pDNA compete with each other in order to bind to an acetylcholine receptor in the neuron cell. In addition, when 10 μg of RVG peptide was present, the genetic expression of the BPEI-SS-PEG-RVG/polynucleotide complex was reduced in Neuro2a cells by about 10 times or more than that of BPEI-SS-MPEG. This means that the polypeptide of a polypeptide delivery system is delivered to the neuron cell through specific bonding of a receptor of Neuro2a cell to RVG peptide.

EXAMPLE 7

Evaluation of in vivo Target Directivity of Synthesized Polynucleotide Delivery System/Polynucleotide Complex A mouse model was used to evaluate in vivo target directivity of a polynucleotide delivery system/polynucleotide complex synthesized (FIG. 7). A BPEI-SS-PEG-RVG/polynucleotide complex was intravenously injected into the tail of a mouse, and all organs including the brain were removed to measure the genetic expression efficiency.

30 μg of pDNA encoding the red fluorescence protein (CMV-RFP) was used on in vivo studies at a ratio of pDNA to the delivery system of 1:1. The pDNA was incubated at room temperature for 15 min to prepare a complex, and then the reaction mixture was injected into the tail vein of a 7-week old male BALB/c rat (n=3). After 24 hours of injection of the complex, organs including the brain were separated and placed in an in vivo imaging system (IVIS: Caliper Life Sciences, Hopkinton, Mass., USA) with an iced CCD camera mounted. Fluorescence signals from the separate organs were obtained at an integration time of 1 sec. Light emitted from each organ was collected with aRFP filter. The filter set used during fluorescence imaging was dsRed (excitation wavelength: 500 to 550 nm) with one f/stop (aperture size) and dsRed (excitation wavelength: 575 to 650 nm), and other experimental apparatus conditions were as follows: image acquisition time (1 sec) and Binning (2). The fluorescence signal obtained by region of interest (ROI) analysis was semi-quantitatively calculated as follows; ROI value=ratio of BPEI-SS-PEG-RVG (or BPEI-SS-MPEG)-introduced brain to the normal brain/ratio of BPEI-SS-PEG-RVG (or BPEI-SS-MPEG)-introduced brain to the normal muscle.

Figure 7A:
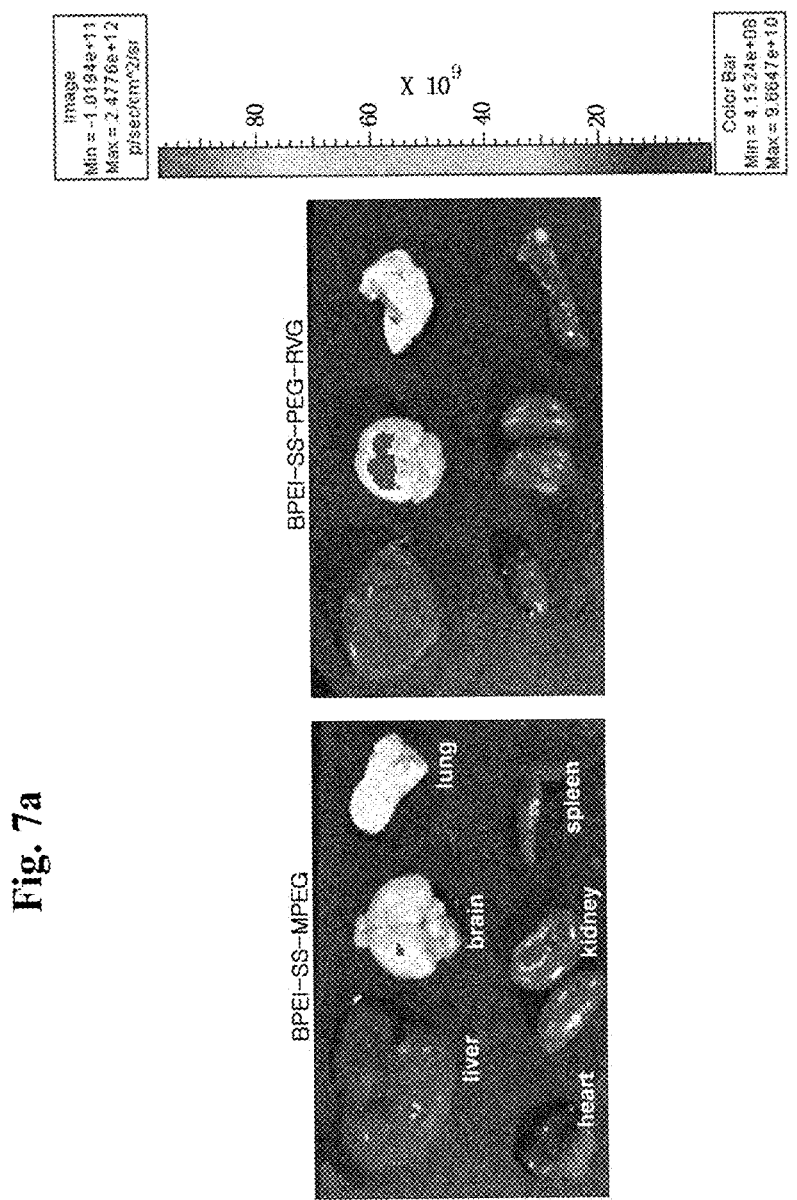
Figure 7B:
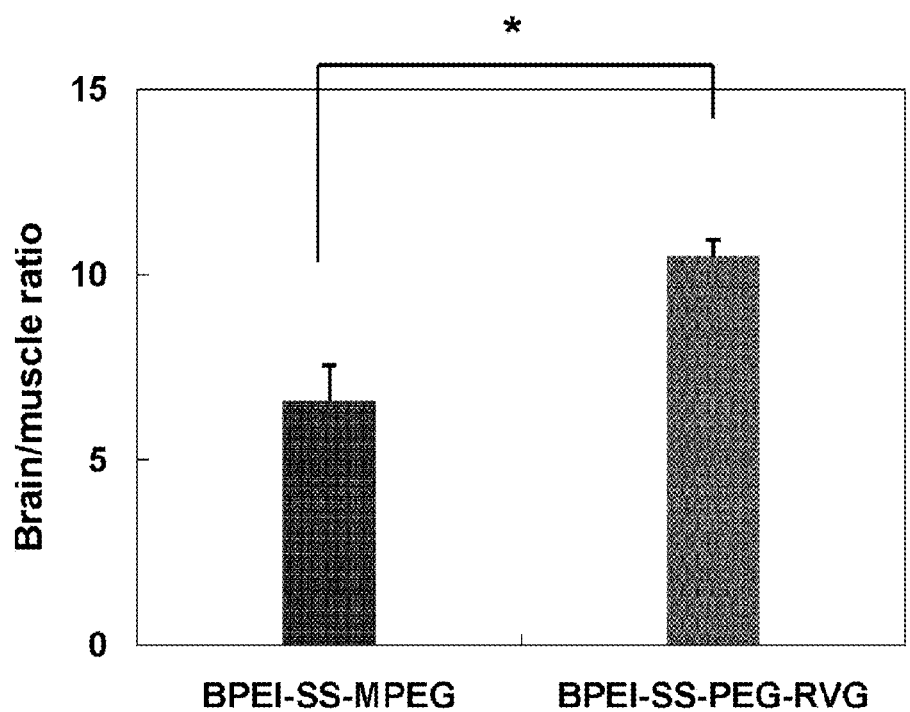

It was confirmed that the genetic expression in the brain of a mouse treated with a BPEI-SS-MPEG/polynucleotide complex was insignificant while the BPEI-SS-PEG-RVG/polynucleotide complex exhibited very high genetic expression efficiency in the brain (FIG. 7a). In addition, the present inventors directly made up a ROI on optical signals for the brain and muscle obtained from an IVIS optical imaging device and measured the ROI value for the ratio of the brain and muscle to confirm that the expression of the RFP gene in the brain region into which BPEI-SS-PEG-RVG had been injected was higher by 1.3 times than that of a control (FIG. 7b).

A polynucleotide delivery system of the present invention has a lower toxicity in a cell and may deliver polynucleotides to a target cell efficiently and safely.

While the present invention has been particularly shown and described with reference to exemplary embodiments thereof, it will be understood by those of ordinary skill in the art that various changes in form and details may be made therein without departing from the spirit and scope of the present invention as defined by the following claims.

SEQUENCE LISTING FREE TEXT

SEQ ID NO 1
Tyr Thr Ile Trp Met Pro Glu Asn Pro Arg Pro Gly Thr Pro Cys 15
Asp Ile Phe Thr Asn Ser Arg Gly Lys Phe Arg Ala Ser Asn Gly 3

The invention claimed is:

1. A polynucleotide delivery system comprising a polyethyleneimine (PEI) to which a rabies virus glycoprotein (RVG) peptide is bound, wherein the polyethyleneimine (PEI) comprises a disulfide bond, wherein a non-peptidic polymer is further bound between the RVG peptide and the polyethyleneimine.

2. The system of claim 1, wherein the non-peptidic polymer is selected from the group consisting of polyethylene glycol, polypropylene glycol, copolymers of ethylene glycol and propylene glycol, polyoxyethylated polyols, polyvinyl alcohol, polysaccharides, dextran, polyvinyl ethyl ether, polylactic acid (PLA), polylactic-glycolic acid (PLGA), lipid polymers, chitins, hyaluronic acid, and a combination thereof.

3. The system of claim 1, wherein the cationic polymer comprises a disulfide bond and the RVG peptide comprises an amino acid sequence of SEQ ID NO. 1.

4. The system of claim 1, wherein the non-peptidic polymer is polyethylene glycol.

5. The system of claim 1, further comprising a polynucleotide selected from the group consisting of gDNA, cDNA, pDNA, mRNA, tRNA, rRNA, siRNA, miRNA, and antisense nucleotide.

6. A method of delivering polynucleotides to a target cell, the method comprising:

binding polynucleotides to the polynucleotide delivery system of claim 1; and contacting the delivery system to which the polynucleotide is bound with the target cell.

7. The method of claim 6, wherein the target cell is an acetylcholine receptor, homologues of the acetylcholine receptor, or a cell expressing polypeptide fragments of the acetylcholine receptor.

8. A method of delivering polynucleotides to a target cell, the method comprising:

binding polynucleotides to the polynucleotide delivery system of claim 2; and contacting the delivery system to which the polynucleotide is bound with the target cell.

9. A method of delivering polynucleotides to a target cell, the method comprising:

binding polynucleotides to the polynucleotide delivery system of claim 3; and contacting the delivery system to which the polynucleotide is bound with the target cell.

10. A method of delivering polynucleotides to a target cell, the method comprising:

binding polynucleotides to the polynucleotide delivery system of claim 4; and contacting the delivery system to which the polynucleotide is bound with the target cell.

11. The method of claim 8, wherein the target cell is an acetylcholine receptor, homologues of the acetylcholine receptor, or a cell expressing polypeptide fragments of the acetylcholine receptor.

12. The method of claim 9, wherein the target cell is an acetylcholine receptor, homologues of the acetylcholine receptor, or a cell expressing polypeptide fragments of the acetylcholine receptor.

13. The method of claim 10, wherein the target cell is an acetylcholine receptor, homologues of the acetylcholine receptor, or a cell expressing polypeptide fragments of the acetylcholine receptor.

* * * * *

SEQUENCE LISTING

```
<160> NUMBER OF SEQ ID NOS: 1

<210> SEQ ID NO 1
<211> LENGTH: 30
<212> TYPE: PRT
<213> ORGANISM: Rabies virus

<400> SEQUENCE: 1

Tyr Thr Ile Trp Met Pro Glu Asn Pro Arg Pro Gly Thr Pro Cys Asp
1               5                   10                  15
```

-continued

```
Ile Phe Thr Asn Ser Arg Gly Lys Phe Arg Ala Ser Asn Gly
            20                  25                  30
```